(12) United States Patent
Avalakki et al.

(10) Patent No.: US 9,139,856 B2
(45) Date of Patent: Sep. 22, 2015

(54) PROCESS FOR PRODUCTION OF GALACTOOLIGOSACCHARIDES (GOS)

(75) Inventors: Uday Kashinath Avalakki, Pune (IN); Palamalai Maheswaran, Pune (IN); Rengarajan Saravanan, Pune (IN)

(73) Assignee: TATA CHEMICALS LTD., Mumbai (IN)

( * ) Notice: Subject to any disclaimer, the term of this patent is extended or adjusted under 35 U.S.C. 154(b) by 409 days.

(21) Appl. No.: 12/922,283

(22) PCT Filed: Mar. 12, 2009

(86) PCT No.: PCT/IB2009/051027
§ 371 (c)(1),
(2), (4) Date: Nov. 2, 2010

(87) PCT Pub. No.: WO2009/113030
PCT Pub. Date: Sep. 17, 2009

(65) Prior Publication Data
US 2011/0065152 A1 Mar. 17, 2011

(30) Foreign Application Priority Data

Mar. 12, 2008 (IN) ............................ 502/MUM/2008
Mar. 14, 2008 (IN) ............................ 520/MUM/2008

(51) Int. Cl.
*C12P 19/00* (2006.01)
*C12P 19/14* (2006.01)
*C12P 19/04* (2006.01)

(52) U.S. Cl.
CPC *C12P 19/14* (2013.01); *C12P 19/04* (2013.01)

(58) Field of Classification Search
CPC ........... A23V 2250/28; A61K 2300/00; A61K 31/702; A23L 1/2363; C12Y 302/01023; C12N 9/2471; C12N 9/2468; C12N 9/38; C12P 19/14; C12P 19/04; C12R 1/01; C07H 3/06
See application file for complete search history.

(56) References Cited

U.S. PATENT DOCUMENTS

| 716,451 A | 12/1902 | Mentz |
| 4,572,897 A | 2/1986 | Amotz et al. |
| 5,032,509 A | 7/1991 | Matsumoto et al. |
| 5,034,324 A | 7/1991 | Shinozaki et al. |
| 5,070,019 A | 12/1991 | Hill |
| 5,093,253 A | 3/1992 | Nolan |
| 5,175,093 A | 12/1992 | Seifert |
| 5,288,632 A | 2/1994 | Pannell |
| 5,759,578 A | 6/1998 | Soon-Shiong et al. |
| 5,766,907 A | 6/1998 | Chang et al. |
| 5,939,294 A | 8/1999 | Sarkki et al. |
| 2003/0022844 A1* | 1/2003 | Bertelsen et al. ............... 514/23 |
| 2007/0274955 A1* | 11/2007 | Gibson et al. ............... 424/93.4 |

FOREIGN PATENT DOCUMENTS

| EP | 0 272 095 A2 | 6/1988 |
| JP | 56-113289 | 9/1981 |
| JP | 58-15243 | 1/1983 |
| JP | 2005-042037 | 2/2005 |
| WO | WO 99/53088 A | 10/1999 |
| WO | WO 2005/003329 A | 1/2005 |

OTHER PUBLICATIONS

Cho et al. Purification and biochemical properties of a galactooligosaccharide producing B-galactosidase from *Bullera singularis*, Biotechnology Letters 25; 2107-2111, 2003.*
Cho et al. Purification and biochemical properties of a galactooligosaccharide producing beta-galactosidase from *Bullera singularis*, Biotechnology Letters (2003.*
Gorin et al. The structures of galactosyl-lactose and galactobiosyl-lactose produced from lactose by *Sporobolomyces singularis*, Canadian Journal of Chemistry (1964), 42: 1341-1344.*
Lewandoska et al., "Ethanol Production From Lactose in a Fermentation/Pervaporation System," Journal of Food Engineering, vol. 79, pp. 430-437 (2007).
Staniszewski et al., "Ethanol Production From Whey in Bioreactor with Co-immobilized Enzyme and Yeast Cells Followed by Pervaporative Recovery of Product—Kinetic Model Predictions," Journal of Food Engineering, vol. 82, pp. 618-628 (2007).
Jianlong et al., "Immobilization of Microbial Cells Using Polyvinyl Alcohol (PVA)—Polyacrylamide Gels," Biotechnology Techniques, vol. 9, No. 3, pp. 203-208 (Mar. 1995).
Axelsson et al., "Economic Evaluation of the Hydrolysis of Lactose Using Immobilized β-Galactosidase," Applied Biochemistry and Biotechnology, vol. 24, No. 25, pp. 679-693 (1991).
Axelsson et al., "Performance of Batch and Continuous Reactors with Coimmobilized Yeast and Beta-galactosidase," Journal of Chemical Technology and Biotechnology, vol. 52, Issue 2 pp. 227-241 (1991).
Tanaka et al., "Ethanol Production From Starch by a Coimmobilized Mixed Culture System of *Aspergillus awamori* and *Zymomonas mobilis*," Biotechnology and Bioengineering, vol. XXVIII, pp. 1761-1768 (1986).

(Continued)

*Primary Examiner* — Iqbal H Chowdhury
(74) *Attorney, Agent, or Firm* — Jenkins, Wilson, Taylor & Hunt, P.A.

(57) ABSTRACT

The present invention deals with an improved process for the production of high yield of pure Galactooligosaccharides using microbial whole cells in a reactor with cross flow hollow fiber microfiltration system. The process is economical as cell biomass is used repeatedly and eliminated the need to carry out downstream processing for the removal of mono and disaccharides from the final product.

11 Claims, 3 Drawing Sheets

(56) References Cited

OTHER PUBLICATIONS

Birnbaum et al., "Covalent Stablization of Alginate Gel for the Entrapment of Living Whole Cells," Biotechnology Letters, vol. 3, No. 3, pp. 393-400 (1981).
International Search Report for International Application No. PCT/IB2009/051027 (Nov. 9, 2009).
Pruksasri, "Production and Separation of Galacto-Oligosaccharides from Lactose by β-Galactosidase Immobilized on Nanofiltration Membranes," Abstract of Thesis 2007 (Retrieved from the Internet on Oct. 26, 2009).
Sakai et al., "Repeated-Batch Production of Galactooligosaccharides from Lactose at High Concentration by Using Alginate-Immobilized Cells of *Sporobolomyces singularis* YIT 1004," Journal of General and Applied Microbiology, vol. 54, pp. 285-293 (Oct. 2008).
Li et al., "Production of Non-Monosaccharide and High-Purity Galactooligosaccharides by Immobilized Enzyme Catalysis and Fermentation with Immobilized Yeast Cells," Process Biochemistry, vol. 43, pp. 896-899 (Oct. 22, 2008).
Ishikawa et al., "Indentification, Cloning, and Characterization of a *Sporobolomyces singularis* β-Galactosidase-like Enzyme Involved in Galacto-Oligosaccharide Production," Journal of Bioscience and Bioengineering, vol. 99, No. 4, pp. 331-339 (2005).
Tzortiz et al., "A Novel Galactooligosaccharide Mixture Increases the *Bifidobacterial* Population Numbers in a Continuous In Vitro Fermentation System and in the Proximal Colonic Contents of Pigs In Vitro," The Journal of Nutrition, vol. 135, No. 7, pp. 1726-1731 (Jul. 2005).
Goulas et al., "Purification of Oligosaccharides by Nanofiltration," Journal of Membrane Science, vol. 209, pp. 321-335 (2002).
Akiyama et al., "Production of Galactooligosaccharides from Lactose Using a β-Glucosidase from *Thermus* sp. Z-1," Bioscience, Biotechnology, and Biochemistry, vol. 65, No. 2, pp. 438-441 (2001).
Jorgensen et al., "High-efficiency Synthesis of Oligosaccharides with a Truncated β-galactosidase from *Bifidobacterium bifidum*," Applied Microbiology and Biotechnology, vol. 57, pp. 647-652 (Dec. 2001).
Rabiu et al., "Synthesis and Fermentation Properties of Novel-Galacto-Oligosaccharides by β-Galactosidases from *Bifidobacterium* Species," Applied and Environmental Microbiology, vol. 67, No. 6, pp. 2526-2530 (Jun. 2001).
Kiss et al., "Extractive Fermentation of Ethanol Using Alginate Gel Co-entrapped Yeast Cells (*Saccharomyces bayanus*) and Lipase Enzyme," Acta Alimentaria, ISN 0139-3006, vol. 28, No. 1, pp. 49-57 (1999).
Shin et al., "Continuous Production of Galacto-Oligosaccharides from Lactose by *Bullera singularis* β-Galactosidase Immobilized in Chitosan Beads," Process Biochemistry, vol. 33, No. 8, pp. 787-792 (1998).
Yuan et al., "Coimmobilization of *Gluconobacter oxydans* and *Bacillus cereus* for Bioconversion of 2-Keto-L-gulonic Acid," Annals of the New York Academy of Sciences, vol. 672, pp. 628-633 (Nov. 1992).
Notice of Grant for Indian Patent Application No. 520/MUM/2008 (Jun. 29, 2012).
Notice of Grant for Indian Patent Application No. 502/MUM/2008 (Jun. 29, 2012).
Hearing Notice for Indian Patent Application No. 520/MUM/2008 (Apr. 30, 2012).
Hearing Notice for Indian Patent Application No. 502/MUM/2008 (Apr. 30, 2012).
First Examination Report for Indian Patent Application No. 520/MUM/2008 (Mar. 23, 2011).
First Examination Report for Indian Patent Application No. 502/MUM/2008 (Mar. 21, 2011).

* cited by examiner

PROCESS FOR PRODUCTION OF GALACTOOLIGOSACCHARIDES (GOS)

FIELD OF THE INVENTION

The present invention relates to a process for the production of high purity galactooligosaccharides/oligosaccharides. The present invention more particularly relates to a process for the production of galactooligosaccharides (GOS) by using microbial whole cells employed in a bioreactor with microfiltration membrane system. The novelty of the process includes the reuse of cell biomass in repeated cycles of biotransformation and the production of high purity (>90%) galactooligosaccharides (GOS) without the separation of mono and disaccharides.

BACKGROUND OF THE INVENTION

Galactooligosaccharides find widespread use in the industry as prebiotic compounds. A number of processes have been developed for the production of galactooligosaccharides. Some processes involve the use of µ-galactosidase enzyme obtained from different microbial sources, example *Aspergillus oryzae, Bullera singularis, Candida, Kluveromyces* sp., *Bacillus circulans, Lactobacillus bulgaricus, Streptococcus thermophilus*, and *Bifidobacterium* sp., (Akiyama et. al., 2001, Rabiu et. al., 2001, Tzortiz et. al., 2005, Jorgensen et al., 2001, Shin et. al., 1998, U.S. Pat. No. 5,032,509, EP 0 272 095 A2).

Use β-galactosidase enzyme or whole cells in immobilized matrices in place of free whole cells or enzymes has also been reported (Akiyama et. al., 2001, Rabiu et. al., 2001, Tzortiz et. al., 2005, Jorgensen et al., 2001, Shin et. al., 1998, U.S. Pat. No. 5,032,509, EP 0 272 095 A2). A combination of β-galactosidase enzyme and *Saccharomyces cerevisiae* cells has been co-immobilized in calcium alginate beads to produce ethanol from whey (Axelsson et al., 1991, Lewandoska et al., 2003 and Tanaka et al., 1986). The objective was to cleave lactose to glucose and galactose and thereby yeast can produce more ethanol.

The processes involving immobilized whole cells or enzyme over the free enzyme has certain advantages (1) catalytic power is stabilized (2) the immobilized matrices can be recycled which reduces cost and (3) products can be isolated in a simple manner. However, the use of immobilized enzymes depends upon the cost benefit and technical feasibility factors. In some processes, the extraction and purification of enzyme is costly and in some cases the enzyme denatures after extraction. Under such conditions, the use of immobilized or coimmobilized whole cells has added advantages over the immobilized enzymes (Yuan et al., 1992, Kiss et al., 1999).

The most prevalent method of whole cell immobilization is cell entrapment in hydrocolloids like alginate, carrageenan, polyacrylamide, agarose, gelatin, gellan gum (U.S. Pat. No. 5,175,093, U.S. Pat. No. 5,288,632, U.S. Pat. No. 5,093,253, U.S. Pat. No. 4,572,897, U.S. Pat. No. 5,070,019, U.S. Pat. No. 5,759,578, U.S. Pat. No. 5,939,294 and U.S. Pat. No. 5,034,324, Birnbaum et al., 1981). JP2005042037, JP5815243, and JP56113289 describe the use of polyvinyl alcohol with polyethylene glycol and boric acid as a successfully alternative to other hydrocolloids.

U.S. Pat. No. 5,766,907 mixed microbial cells in calcium chloride solution containing small amount of xanthan gum and then dropped into sodium alginate. The capsule membrane formed by ionic bond between calcium and alginate prevented swelling of the membrane and resulted in a high concentration of microbes within the capsule.

U.S. Pat. No. 5,034,324 discloses that polyvinyl alcohol has a high affinity for microorganisms and provides mechanical strength and durability sufficiently high for use in any reactor, and high resistance to water and chemicals. Jianlong et al., (1995) used acryl amide as polymerizing agent in the polyvinyl alcohol matrix with boric acid as cross-linking agent to overcome the swelling of polyvinyl alcohol gels in aqueous solution.

However use of immobilized cells has following disadvantages;

a. The matrix and Cross linking agents must comply regulatory approval for the use in food grade conditions.
 b. Mechanical stability of immobilized beads with cells is poor
 c. Constraints in the diffusion of substrate and products and hence the efficiency of bioconversion is less than in free cells.
 d. Because of low conversion efficiency, the product separation form unreacted substrate and impurities is a challenging task U.S. Pat. No. 716,451 describe mixing of the saccharide solution, obtained after hydrolysis, with ethanol and passing through activated carbon column to remove the mono and disaccharide components. The galactooligosaccharide component is eluted using pure ethanol. This downstream processing results in substantially pure galactooligosaccharide solution However, this process is not efficient due to the loss in the yield of galactooligosaccharides. Also, it is not economical due to the use of ethanol.

To overcome the limitation of activated carbon column treatment, EP 0 272 095 A2 and U.S. Pat. No. 5,032,509 describe loading of the saccharide solution on a strong cation exchange resin followed by elution of galactooligosaccharides with water at 60 to 80° C. This process can improve the yield of galalctooligosaccharide. However, it is not cost effective because of the use of costly strong cation exchange resin.

Therefore, the need for a cost effective process that results in the production galactooligosaccharides of high purity and yield galactooligosaccharides continues to prevail.

SUMMARY OF THE INVENTION

The main object of the present invention is to provide a process for the production of galactooligosaccharides (GOS) of high purity and yield using whole cells of yeasts in a bioreactor with microfiltration membrane system.

The other object of the present invention is the use of mixed whole cells of yeasts for the production of GOS.

Further object of the invention is to obtain GOS without the use of any costly resins.

Further the present invention provides a color less GOS syrup using carbon polishing along with concentrator.

Furthermore, the present invention provides amorphous powder/crystalline GOS using spray driers/crystallizers.

Accordingly, the present invention provides a process for production of high purity galactooligosaccharides by free cells comprising:

a. growing of a microorganisms producing enzyme for hydrolying sugar to oligosaccharide under optimum medium and conditions to obtain cell biomass of *B. singularis* and *Saccharomyces* sp.,
 b. hydrolysis of lactose and utilization of produced glucose by mixed microbial culture, c. separating galactooligosaccharides from microbial culture using microfiltration membrane system/centrifugation,
d. filtering said galactooligosaccharides using a deep bed filter with cotton and activated carbon/carbon filter at a flow rate of 10-30 mL/min,
e. concentrating galactooligosaccharides at the temperature range of 40-60° C. in vacuum evaporator so as to obtain a syrup having 70-80% dissolved solids,
f. drying said syrup to obtain high purity of galactooligosaccharides in amorphous form powder,
g. crystallizing said amorphous powder to obtain crystalline galactooligosaccharides.

In accordance with one embodiment of the invention, the immobilized whole cells of yeasts are used in a sequential reactor composed of a series of reactors wherein the hydrolysis products from one reactor serve as the feed for the next reactor in the series.

In accordance with another embodiment, the yeast cells are coimmobilized and used in a single reactor.

The present invention eliminates the need for the down stream process for the separation of contaminating saccharides.

This process of coimmobilization of whole cells can be applied to other products such as oligosaccharides, organic acids and other biotechnological process where more than microorganisms are involved.

BRIEF DESCRIPTION OF DRAWINGS

The process described in this invention will become apparent from the drawings given below.

DETAILED DESCRIPTION OF THE INVENTION

Figure 1:
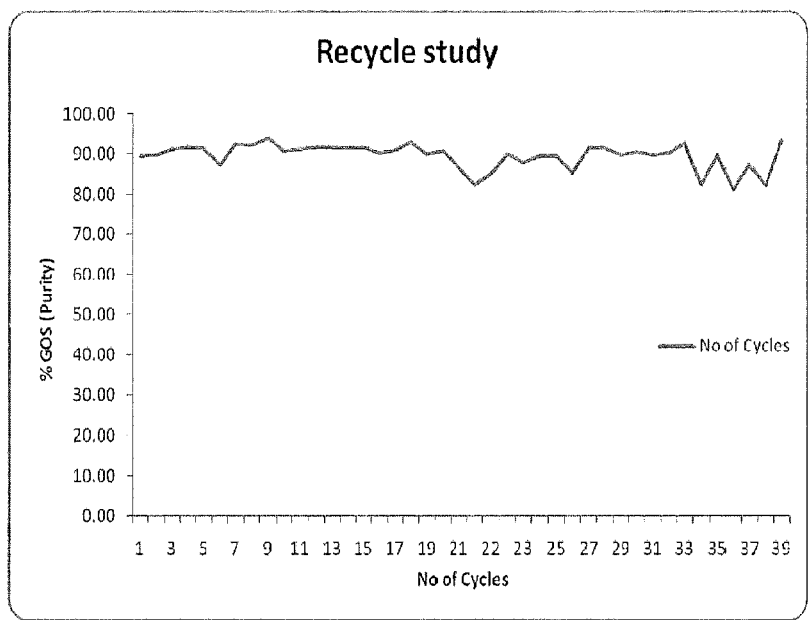
FIG. 1: Reuse of free cells for galactooligosaccharide production.
Figure 2:
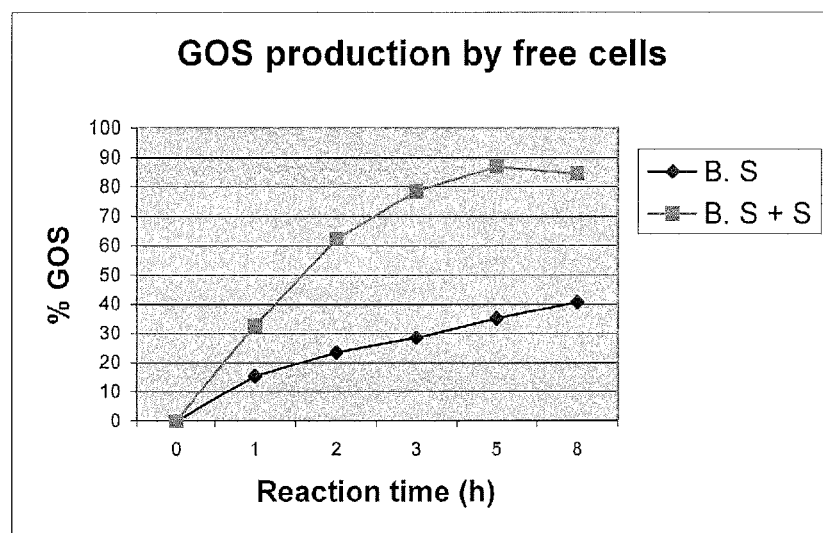
FIG. 2: Production of GOS by free cells of *B. singularis* and mixed cells of *B. singularis* and *Saccharomyces* sp.
Figure 3:
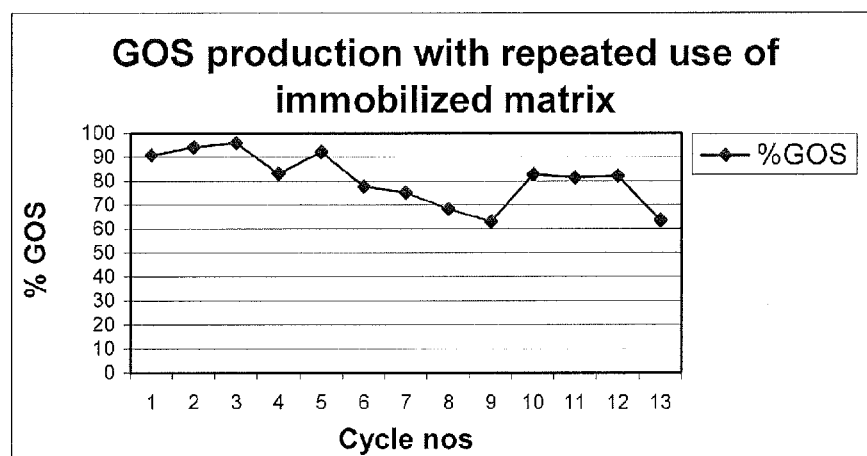
FIG. 3: GOS production by reuse of immobilized matrix.

A novel and improved process for production of high purity galactooligosaccharides by free cells comprises production of cell biomass in shaker flask and/or fermentor using the optimized growth medium, separation of cells from the fermentation media using centrifugation/microfiltration membrane system, use of mixed cultures in a bioreactor for the production of GOS and utilization of glucose produced, estimation of purity of GOS by HPLC using sugar columns, separations of GOS form the microbial cells using centrifugation/microfiltration membrane system, filtration of GOS using a depth carbon filter/deep bed filter having filter media and activated carbon, concentration of GOS to obtain in syrup (70-80% dissolved solids) form, drying/crystallization of GOS to obtain in amorphous/crystalline powder form.

In accordance with the first embodiment, the cell biomass of *B. singularis* and *Saccharomyces* sp were produced in the shaker flask and/or fermentor using the optimized growth medium.

In accordance with the second embodiment, the mixed microbial cultures of *B. singularis* and *Saccharomyces* sp. (1:1 ratio dry wt. basis).

In accordance with the third embodiment, mixed microbial cell biomass was transferred to a reactor tank fitted with microfiltration membrane system and hydrolysis is carried using 15-45%, preferably 30% lactose at about 3 to 10 pH, at about 10-60° C., preferably 30° C., in about 12 to 48 hours having agitation speed in the range of about 50 to 200 rpm such that the purity of GOS reached more than 90%. Hydrolyzed mass was circulated through microfiltration to collect permeate (50% of reacted mass) for the downstream process. Fresh batch of lactose solution (30%) was charged into the reactor for the second cycle of hydrolysis. Hydrolysis cycles were repeated by adding the said additional biomass to compensate the desired conversion efficiency i.e. until there is 10-20% drop in efficiency even with the addition of additional of 10% cell biomass.

The filtration of galactooligosaccharides is done by using a deep bed filter with cotton and activated carbon/carbon filter at a flow rate of 10-30 ml/min, preferably 20 ml/min.

In accordance with the fourth embodiment, permeate was passed through a carbon polisher and then through 0.2 micron microfiltration to remove the color and suspended carbon particles.

In accordance with the fifth embodiment, the carbon polished hydrolyzed solution was passed through a concentrator at 40-60° C., in vacuum to obtain syrup of 70-80% dissolved solid content.

In accordance with the sixth embodiment of the invention, the carbon polished hydrolyzed solution was passed through a spray drier under pressure through the nozzles in the temperature range of about 110-140° C. to obtain the dry powder.

The present invention is further illustrated in the following examples. However, the scope of the invention should not be limited to these examples as the person skilled in the art can easily vary the proportion of the ingredients and combinations.

Example 1

Isolation of Lactose Hydrolyzing *B. singularis* Culture

*B. singularis*, TCL-IC/NUT-1, was isolated from dairy effluents by serial dilution method on Yeast-Malt-Peptone (YMP) medium of the following composition; Yeast extract 0.3%, Malt extract 0.3%, Peptone 0.5%, Dextrose 1% and Lactose 1%, and agar 2.0%, pH 6.5.

Working stock culture: The cultures were streaked on YMP slants and incubated for 48 h at 27° C. These slant cultures were used as working stock culture.

Preparation of inoculum: 50 ml YMP medium in 250 ml flask was inoculated with a loop full of culture from the slants and incubated in a shaker for 48 h at 27° C. at 180 rpm.

Shake flask trials: 150 ml of YMP medium in 500 ml flasks was inoculated with 5% inoculum and incubated on the shaker for 48 h at 27° C. at 180 rpm. The samples from the shake flask were taken aseptically and assayed for GUS production as given in Example 2.

Fermentation trials: 3 l of YMP medium was charged in 5 l fermentor and sterilized. The fermentor was inoculated with 5% inoculum from the shaker flask. Fermentation was carried out at 27° C., pH 4.5, 600 rpm agitation, and with 1 vvm of air to maintain 40-60% dissolved oxygen. The samples from fermentor were taken at 24, 48 and 67 h to determine maximum GOS production as described in Example 2.

Example 2

Assay for Galactooligosaccharide Production 25 ml of the cell suspension from the shaker flask or fermentor was centrifuged to obtain cell pellet. The cell pellet was suspended in 15 ml of 40% lactose solution and kept on shaker at 50° C. and 280 rpm agitation. 0.5 ml of the samples was taken out centrifuged to remove the cell biomass. The supernatant was diluted 50 times with milli Q water. 5 μl of diluted samples was injected in to the HPLC system.

HPLC analysis: The concentration of sugars (glucose, galactose, lactose, and Galactooligosaccharides) was determined by HPLC. The HPLC (Waters 717) system consisted of refractive index detector (waters W2467) and carbohydrate column Phenomenex (RNM 00h-0316, REZEX 300 mm L×7.5 mm, pore size 8 u) ID column. The column temperature was maintained at 80° C. Water was used as mobile solvent with flow rate of 0.5 ml/min. Galactooligosaccharides and other sugars were determined as weight percentage of total sugars based on the area of peak.

Experiment 3

Production of Galactooligosaccharides by Free Cells of *B. singularis*

25 ml of cell suspension from the shaker flask or fermentor was centrifuged to obtain cell pellet. The cell pellet was suspended in 15 ml of 30% lactose solution and kept on shaker at 50° C. and 180-rpm agitation.

TABLE 1

Galactooligosaccharide production by free cell of *B. singularis*.

| Reaction time (h) | % GOS |
|---|---|
| 1 | 16.00 |
| 3 | 25.40 |
| 6 | 35.20 |

The results in Table 1 indicate the galactooligosaccharides production is higher than reported by Yang et al., while it is same as reported by Shin et al 199

Experiment 4

Effect of Lactose Concentration on the Galactooligosaccharide Production by Whole Cells of *B. singularis*

100 g of cured beads were suspended in 120 ml of 20 and 40% aqueous lactose solution, pH 4.5, for hydrolysis. Hydrolysis was carried out on shaker flask at 180 rpm agitation and 30° C. Half a milliliter sample is taken at different time intervals and processed for galactooligosaccharide by HPLC.

TABLE 2

Effect of lactose concentration on the galactooligosaccharide production by whole cells of *B. singularis*

| Lactose % | GOS % | Glucose % | Lactose % |
|---|---|---|---|
| 20 | 40.96 | 15.51 | 43.53 |
| 30 | 41.80 | 16.20 | 42.00 |
| 40 | 42.52 | 17.20 | 40.60 |

There was no significant difference in the GOS production with the increase in lacose concentration from 20 to 40% (Table 2).

Experiment 5

Kinetics of GOS Production

TABLE 3

Kinetics of galactooligosaccharide production by whole cells of *B. singularis*

| Reaction time (h) | % sugar | | |
|---|---|---|---|
| | GOS | Glucose | Lactose |
| 2 | 17.00 | 6.06 | 75.85 |
| 6 | 28.71 | 11.54 | 59.57 |
| 9 | 35.77 | 2.42 | 51.27 |
| 12 | 41.0 | 17.02 | 40.69 |

The results of Table 3 indicate that lower the concentration of lactose higher the galactooligosaccharide production. Low galactooligosaccharide production at high lactose concentration may be due to substrate inhibition and/or glucose produced during hydrolysis of lactose.

Experiment 6

Isolation of *Saccharomyces* sp.

This strain was isolated from contaminated dextrose syrup on MYGP medium composed of Malt extract 0.3%, Yeast extract 0.3%, Glucose 1.0%, Peptone 0.5% and agar 2.0%, pH 6.4. The strain was characterized for the utilization of glucose and lactose. The strain, TCL-IC/NUT-2, growing only in presence of glucose and not in the presence of lactose was selected (lac⁻, glc⁺). Production of cell biomass from this strain in shaker flask and fermentor was similar to *B. singularis* except for the growth medium.

Experiment 7

Hydrolysis of Lactose and Glucose by *Saccharomyces* sp.

25 ml of the cell suspension from the shaker flask or fermentor was centrifuged to obtain cell pellet. The cell pellet was suspended in 15 ml of 20% lactose and 2% glucose solution and kept on shaker at 50° C. and 180 rpm agitation. The samples were taken at regular intervals of time and assayed for residual lactose and glucose concentration by HPLC as described in Example 2.

TABLE 4

Hydrolysis of lactose and glucose by *Saccharomyces* sp.

| Hydrolysis time (h) | Residual sugar (%) | |
|---|---|---|
| | Lactose | Glucose |
| 0 | 100 | 100 |
| 3 | 86.44 | 5.21 |
| 5 | 92.61 | 4.75 |

The results of Table 4 show that *Saccharomyces* sp. utilize glucose preferably compared to lactose. Thus, the culture has been characterized as lac⁻, glc⁺

Experiment 8

Effect of Mixed Free Cells of *B. singularis* and *Saccharomyces* sp.

25 ml of the cell suspension of *B. singularis* and 25 ml suspension of *Saccharomyces* sp from the shaker flask or fermentor was mixed and centrifuged to obtain cell pellet. The cell pellet was suspended in 15 ml of 30% lactose solution and kept on shaker at 30° C. and 180 rpm agitation. Half a milliliter sample was taken at different time intervals and processed for galactooligosaccharide by HPLC.

TABLE 5

Production of Galactooligosaccharide by mixed free cells of *B. singularis* and *Saccharomyces* Sp.

| Hydrolysis time (h) | % GOS production |
|---|---|
| 1 | 50.80 |
| 2 | 76.04 |
| 4 | 77.95 |
| 5 | 74.85 |
| 7 | 70.26 |

The results of Table 5 indicate that purity of GOS increased to 70.26% in 7 has a compared to 35% GOS with *B. singularis* (Table 3).

Experiment 9

Production of Galactooligosaccharides by Mixed Cells in a Reactor with Microfiltration System The whole cells of *B. singularis* and *Sacccahromyces* Sp. were mixed in equal concentrations (1:1 dry weight basis) with 30% w/w lactose solution in a reactor. The reaction temperature was maintained at 30° C. After 24 h samples were taken and analyzed for GOS concentration (Table 6)

| | % Sugar | | | |
|---|---|---|---|---|
| Experiments | GOS | Lactose | Glucose | Galactose |
| Expt 1 | 91.49 | 8.51 | 0.00 | 0.00 |
| Expt 2 | 91.36 | 8.64 | 0.00 | 0.000.00 |
| Expt 3 | 90.69 | 9.31 | 0.00 | |

Example 10

Repeated Cycles of GOS Production

Whole cells of *B. singularis* and *Saccharomyces* sp. were mixed as in the Example 9 in reactor attached with cross flow microfiltration system with membrane made up of Polyether sulfonate of 0.5 micron pore size, 340 mm lumen dia (ID) and area of 0.6 meter. When the purity of GOS reached more than 90%, 50% percent of the solution was removed by passing through cross flow microfiltration system through permeate and fresh lactose solution 30% was added to make up the volume in the reactor to start the next cycle. The cycle was repeated until there was 10% drop in the purity of GOS The results from FIG. 1 indicated that more than 90% pure GOS was produced in the reactor in 39 repeated cycles wherein the cell biomass was reused in the GOS production.

Experiment 11

Concentration of GOS

The solution obtained from the experiment 10 was pooled and filtered through activated carbon pad to remove the color. The carbon polished hydrolyzed solution is passed through a concentrator at 40-60° C., in vacuum to obtain syrup of 70-80% dissolved solid content.

Experiment 12

Spray Drying of GOS

The dilute galactooligosaccharides is sprayed in a spray direr (Bovan make) of capacity 4 kg/h was used for making GOS powder. Five liters of dilute GOS of having 25° Brix was sparged at rate of 40 m/min through the nozzle. The other process parameter maintained apart form the flow rate is temperature in the range of 125-130° C. under pressure. The obtained product had shown a white color powder.

We claim:

1. A process for producing high purity galactooligosaccharides (GOS) by free cells, the process comprising:
   a) growing a mixed microbial culture of *Bullera singularis* and *Saccharomyces* sp. in the presence of lactose;
   b) hydrolyzing the lactose and using the glucose produced thereby by the *B. singularis* and/or the *Saccharomyces* sp. present in the mixed microbial culture;
   c) separating GOS from the mixed microbial culture using a microfiltration membrane system or centrifugation;
   d) filtering the GOS using a deep bed filter with cotton and activated carbon or carbon filter at a flow rate of 10-30 ml/min;
   e) passing permeate through a carbon polisher followed by a 0.2 micron microfiltration membrane system to remove color and suspended carbon particles;
   f) concentrating the GOS at a temperature range of 40-60° C. in a vacuum evaporator to obtain a syrup having 70-80% dissolved solids;
   g) drying the syrup to obtain high purity GOS in an amorphous form powder; and
   h) crystallizing the amorphous powder to obtain crystalline GOS.

2. The process as claimed in claim 1, wherein the *B. singularis* and the *Saccharomyces* sp. are isolated from whey effluent and contaminated sugar solution, respectively.

3. The process as claimed in claim 1, wherein the *Saccharomyces* sp. is lac– glu+ or gal+.

4. The process as claimed in claim 1, wherein said growing step occurs in a shaker flask and by fermentation.

5. The process as claimed in claim 1, wherein the ratio of *B. singularis* to *Saccharomyces* sp. present in the mixed microbial culture is in the range of 1:1 to 1:2 on a dry weight basis.

6. The process as claimed in claim 1, wherein the hydrolyzing step is carried out in a bioreactor using an about 15 to about 45% lactose solution at a pH of about 3 to about 10 and a temperature of about 10° C. to 60° C. for about 12 to 48 hours and an agitation speed of about 50 to 200 rpm.

7. The process as claimed in claim 1, wherein the hydrolyzing step is repeated by adding additional biomass to compensate the desired conversion efficiency.

8. The process as claimed in claim 1, further comprising passing the carbon polished permeate through a concentrator at 40-60° C., in vacuum, to obtain a syrup of 70-80° A) dissolved solid content.

9. The process as claimed in claim 1, wherein the 0.2 micron microfiltration membrane system comprises a membrane selected from the group consisting of a polyether sulfone (PES) membrane, a polytetrafluoroethylene (PTFE) membrane, a regenerated cellulose or ceramic hallow fiber membrane, and a tangential flow filtration (TFF) cassette membrane.

10. The process as claimed in claim 1, further comprising recycling the mixed microbial culture in a reactor attached with a cross flow microfiltration system with membrane.

11. The process as claimed in claim 6, wherein the lactose solution is about 30% lactose.

\* \* \* \* \*